United States Patent [19]

Huber

[11] Patent Number: 4,740,356

[45] Date of Patent: Apr. 26, 1988

[54] DEVICE FOR PRODUCING A GASEOUS MEASURING SAMPLE FOR ATOMIC ABSORPTION SPECTROSCOPY

[75] Inventor: Bernhard W. Huber, Überlingen, Fed. Rep. of Germany

[73] Assignee: The Perkin-Elmer Corporation, Norwalk, Conn.

[21] Appl. No.: 821,651

[22] Filed: Jan. 23, 1986

Related U.S. Application Data

[63] Continuation of Ser. No. 502,994, Jun. 10, 1983, abandoned.

[51] Int. Cl.[4] ............................................. G01N 27/66
[52] U.S. Cl. ................................. 422/81; 137/624.18; 141/21; 141/39; 422/80; 422/112; 422/116; 436/43
[58] Field of Search ............ 422/78, 80, 81, 112, 422/116, 64; 137/624.18, 624.2; 141/30, 39, 21; 436/43

[56] References Cited

U.S. PATENT DOCUMENTS

| | | | |
|---|---|---|---|
| 3,983,864 | 10/1976 | Sielaff et al. | 128/2 G |
| 4,003,257 | 1/1977 | Fletcher et al. | 73/23.1 |
| 4,148,610 | 4/1979 | Miller, Jr. et al. | 422/81 |
| 4,187,991 | 2/1980 | Poli | 241/33 |
| 4,273,742 | 6/1981 | Huber et al. | 422/80 |
| 4,294,804 | 10/1981 | Baran | 422/116 |

Primary Examiner—Michael S. Marcus
Attorney, Agent, or Firm—Ronald G. Cummings; Edwin T. Grimes

[57] ABSTRACT

Inert gas is supplied to a closed reagent reservoir for reagent dosing in producing gaseous measuring samples according to the "hydride method". Thereby, reagent is pressed into a sample vessel through a reagent dosing conduit. A manometric switch is provided at the inert gas connecting conduit to produce a defined reagent flow, by means of which manometric switch a valve located in the connecting conduit is driven into its closed position, if a preset pressure has been reached.

2 Claims, 1 Drawing Sheet

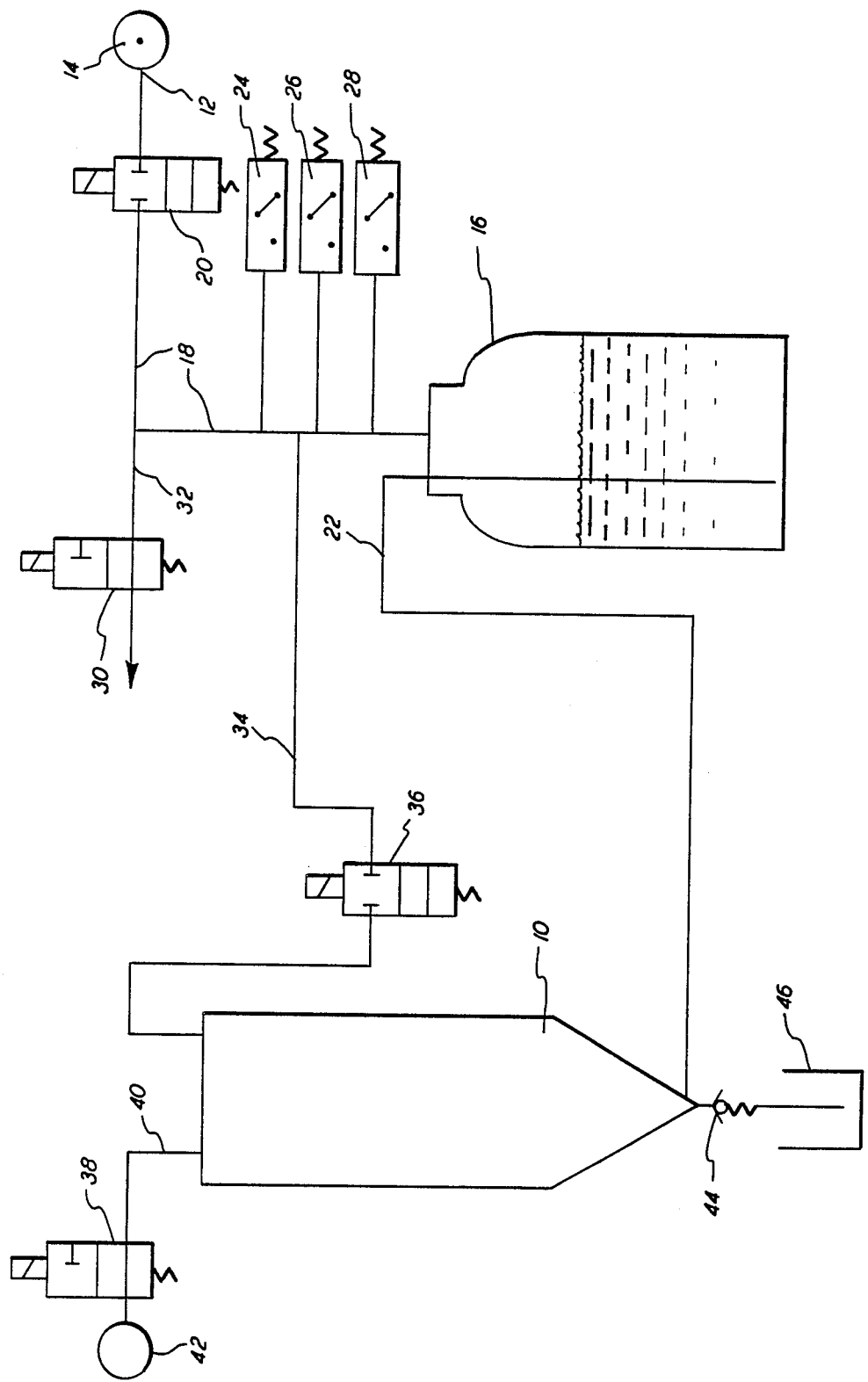

DEVICE FOR PRODUCING A GASEOUS MEASURING SAMPLE FOR ATOMIC ABSORPTION SPECTROSCOPY

This application is a continuation of application Ser. No. 502,994, filed June 10, 1983, abandoned.

BACKGROUND OF THE INVENTION

The present invention generally relates to a device for producing a gaseous measuring sample from a sample liquid in a sample vessel for transfer into the flame or measuring cuvette of an atomic absorption spectrometer, and, in particular, relates to such a device including means for equalizing the differential pressure across the reagent dosing conduit to interrupt the adding of reagent.

The production of volatile hydrides of a sought element, e.g. arsenic or selenium, in a sample vessel by adding a strong reducing agent, such as a reagent, thereto is known. The volatile hydrides so produced are then transferred to a heated measuring cuvette of an atomic absorption spectrometer via an inert gas flow and are therein thermally decomposed. The sought element thus appears in its atomic state in the measuring cuvette, and its atomic absorption may be measured. It is also possible to release a volatile substance from its compounds by the reagent, which volatile substance is carried away by the inert gas flow such that the atomic absorption of this volatile substance may be determined in the measuring cuvette.

In order to perform this analysis an inert gas flow is initially passed through the sample vessel and the measuring cuvette via an inert gas feed conduit. These components are flushed by the inert gas, and the air is displaced from the system. Subsequently, a reagent, e.g. $NaBH_4$, is added to the sample liquid, whereby a volatile measuring sample e.g. $AsH_3$, is produced. This volatile measuring sample is transferred to the heated measuring cuvette by the inert gas flow and is thermally decomposed therein such that an "atomic cloud" of the sought element is formed.

One such known reagent adding device (German Auslegeschrift No. 27.18.381 corresponding to Huber, U.S. Pat. No. 4,208,372) contains a gaseously sealed reagent reservoir. A connecting conduit leads from an inert gas feed conduit to the reagent reservoir and permits a build up of pressure therein. A reagent dosing conduit leads from the bottom of the reagent reservoir to the sample vessel. If the stop valve in the inert gas feed conduit is closed, reagent liquid is displaced from the reagent reservoir by the inert gas pressure and is pressed into the sample vessel through the reagent dosing conduit. If the stop valve is opened, pressure equalization between sample vessel and reagent reservoir is effected such that the delivery of reagent is interrupted.

The German Auslegeschrift No. 27.35.281 (corresponding to Huber, U.S. Pat. No. 4,208,372) shows one arrangement for ensuring a good mixing of reagent and sample liquid by leading the reagent into the lower part of the sample vessel. Of course, measures are taken to prevent the reagent liquid from continuously flowing or to prevent the sample from flowing back into the reagent reservoir.

From the German Offenlegungsschrift No. 27.29.744 (corresponding to Huber, U.S. Pat. No. 4,230,665) a device is known which permits automatic analysis of a series of sample liquids one-by-one in producing a gaseous sample from each of these sample liquids and measuring it by measuring the atomic absorption.

The individual samples are introduced sequentially into a reaction vessel by means of a sampler. A reagent is added each time by means of a reagent supply device. The resulting gaseous measuring sample is transferred to a heatable measuring cuvette through a carrier gas discharge conduit. The bottom of the reaction vessel includes a valved drain through which the contents of the reaction vessel is discharged into a waste vessel upon completion of the measurement. A program control is arranged to control the reagent supply device, the sampler and the drain valve in accordance with a preset program which program includes a measuring cycle for each sample.

From the German Auslegeschrift No. 28.51.058 (corresponding to Huber et al, U.S. Pat. No. 4,273,742) a modification of this device is known which ensures that the program proceeds to the next measuring cycle only if the reaction vessel or sample vessel is completely empty. To this end, the drain valve is a relief valve which opens in the discharge direction but is biased in the closing direction. A controlled stop valve is located in the carrier gas discharge conduit to the measuring cuvette. A pressure sensor is connected to the carrier gas supply conduit and responds to a predetermined pressure threshold being exceeded. The program control device is arranged to close the stop valve in the carrier gas discharge conduit after the measurement has been made, such that the reaction, or sample vessel, is gaseously sealed. The program control device is arranged to proceed to the next measuring cycle, if the pressure sensor is in its unactuated state after a predetermined time interval. The unactuated state corresponds to a pressure below a preselected threshold pressure valve. After the stop valve in the carrier gas discharge conduit is closed a pressure builds up in the reaction or sample vessel, consequently the relief valve is urged open and the liquid is forced out of the reaction, or sample vessel, into waste vessel. Due to its viscosity, the liquid encounters a flow resistance during discharge which resistance is sufficiently strong that a further pressure increase occurs in the reaction or sample vessel during discharge of the liquid. Thereby, the pressure sensor responds. As soon as the reaction, or sample, vessel is completely emptied, only carrier gas flows through the drain. The pressure in the reaction, or sample, vessel breaks down due to the reduced flow resistance presented by the carrier gas to the drain. The pressure sensor, consequently, returns its unactuated state. The program proceeds to the next measuring cycle only, if this is the case after a preset time interval.

SUMMARY OF THE INVENTION

Accordingly, one object of the present invention is to ensure an exact dosing of the reagent liquid added independently of the level of the reagent reservoir.

This object is achieved, at least in part, by a device including at least one manometric switch disposed downstream of the stop valve which stop valve is disposed in the connecting conduit. The stop valve being actuated in closing sense in response of the manometric switch.

Other objects and advantages will become apparent from the following detailed description read in conjunction with the attached drawing and the claims appended hereto.

BRIEF DESCRIPTION OF THE DRAWING

An exemplary device, embodying the principles of the present invention, is described hereinafter in greater detail with reference to the accompanying drawing, which drawing is a schematic circuit of such a device for producing a gaseous measuring sample from a sample liquid.

DETAILED DESCRIPTION OF THE INVENTION

A reaction, or sample vessel, is designated at numeral 10 in the figure. A sample liquid is supplied to the sample vessel 10 in a known manner, for example in the manner of German Offenlegungsschrift No. 27.29.744. The device includes an inert gas inlet 12 connectable to an inert gas source 14. A reagent liquid is contained in a gaseously sealed reagent reservoir 16. A connecting conduit 18 leads from the inert gas inlet 12 to the reagent reservoir 16 and permits a pressure to build up therein. A stop valve 20 designed as a controlled valve, preferably as a solenoid valve, is disposed in the connecting conduit 18. A reagent dosing conduit 22 leads from the bottom of the reagent reservoir 16 to sample vessel 10. Reagent liquid displaced by the inert gas pressure flows through the reagent dosing conduit 22 to the reaction vessel 10. Means, more fully described below, for equalizing the differential pressure across the reagent dosing conduit 22 is also provided.

Preferably, at least one manometric switch is disposed at the connecting conduit 18 downstream of the stop valve 20 therein. In the preferred embodiment, a plurality of manometric switches 24,26,28 are provided, each of which responds at a different pressure, e.g. at 0.1 bar, 0.2 bar and 0.3 bar. The stop valve 20 is actuated, the closing sense, in response to the manometric switch. In the arrangement having three manometric switches the stop valve 20 is arranged to be controlled selectively by one of these manometric switches 24,26,28. The inert gas pressure at the inert gas inlet 12 is substantially larger than the pressure at which the manometric switch, 24, 26, or 28, controlling the stop valve 20 responds.

This arrangement ensures that the reagent liquid flow flowing through the reagent dosing conduit 22 is, in general, independent of the level of the reagent reservoir 16. After the valve 20 has been opened, the pressure in the reagent reservoir 16, due to the relatively high pressure at the inert gas inlet 12 very quickly increases up to the value at which the manometric switch, e.g. the manometric switch 24, responds and recloses the stop valve 20. Reagent liquid is pressed into the sample vessel 10 through the reagent dosing conduit 22 at this defined pressure (against atmospheric pressure, more fully discussed below). Thus, the reagent liquid flow through the reagent dosing conduit 22 is well-defined. This reagent liquid flow can be adjusted in accordance with the device requirements by the selection of a suitable manometric switch, 24,26 or 28, for controlling the stop value 20.

The means for equalizing the differential pressure across the reagent dosing conduit 22 includes a vent valve 30 designed as a controlled valve, preferably a solenoid valve, which is closed while reagent is added and through which the reagent reservoir 16 is vented to atmosphere to interrupt the delivery or reagent. The vent valve 30 is disposed in a conduit 32 branching off the connecting conduit 18 and ending in, or opening to, the atmosphere. When the stop valve 20 is closed the pressure in the reagent reservoir 16 breaks down and the vent valve 30 opens. In this manner the delivery of reagent to the sample vessel 10 is interrupted.

The connecting conduit 18 is connected to the sample vessel 10 through a carrier gas feed conduit 34 downstream of the stop valve 20. A controlled stop valve 36, preferably a solenoid valve, is disposed in the carrier gas feed conduit 34. Another controlled stop valve 38 is located in a carrier gas discharge conduit 40 leading from the sample vessel 10 to the flame or measuring cuvette 42 of an atomic absorption spectrometer.

At its lower end, the sample vessel 10 is connected to a waste vessel 46 through a biased relief valve 44 which opens in the discharge direction.

The embodiment hereinbefore described operates as follows. To add reagent, the valves 30 and 36 are closed. Valve 38 is open. Thereby, the interior of the sample vessel 10 is vented to atmosphere through the carrier gas discharge conduit 40 and the measuring cuvette. Next, the solenoid valve 20 is opened and the pressure in the reagent reservior 16 increases, as described, to a preset value by the manometric switch e.g. 24. Then the manometric switch 24 actuates the stop valve 20 to close. Then reagent is delivered through the reagent dosing conduit 22 by means of a reagent liquid flow preset by the manometric switch 24. To terminate the delivery of reagent, the vent valve 30 is opened, whereby the reagent reservoir 16 is vented. The same pressure is then present at both ends of the reagent dosing conduit 22.

The manometric switch 24 thereby returns the stop valve 20 to its open position. A control device (not shown) returns the vent valve 30 to its closed position and at the same time, returns the valve 36 to its open position. Now an inert gas flow flows from the inert gas source 14 through the inert gas inlet 12, the stop valve 20, the connecting conduit 18, the inert gas feed conduit 34 and the valve 36 into the sample vessel 10 and, from there, through the inert gas discharge conduit 40, the valve 38 and the measuring cuvette 42 into the open air. Accordingly, volatile compounds or elements which have been formed from the sample liquid due to the adding of the reagent liquid are transferred from the sample vessel 10 into the measuring cuvette 42. Volatile compounds, hydrides, are decomposed by the heated measuring cuvette 42 such that measurement of the atomic absorption can be carried out.

After the measurement has been completed, the stop valve 38 is closed. Furthermore, the control function of the manometric switch, 24,26, or 28, is changed. This can be effected by means of the control device.

Now the inert gas pressure through the connecting conduit 18 and the inert gas feed conduit 34 becomes effective in the sample vessel 10. In the same way, however, the inert gas pressure is effective in the reagent reservoir 16, too, such that there is no flow through the reagent dosing conduit 22. The increasing pressure opens the relief valve 44 and presses the sample and reagent liquid contained in the sample vessel 10 therefrom and into the waste vessel 46. The increase of pressure urges the manometric switch, e.g. 24, to respond as long as the sample vessel 10 is being emptied and the emerging sample and reagent liquid meets a relatively high flow resistance. After the sample vessel 10 has been emptied, only inert gas emerges which meets a substantially reduced flow resistance such that the pressure in the sample vessel drops. Thereby, the manometric switch 24 returns to its initial position. In the changed control function, the manometric switch 24 does not cause the stop valve 20 to close any longer but acts as pressure sensor monitoring the emptying of the sample vessel 10, as illustrated in FIG. 4 of German Auslegeschrift No. 28.51.058. In this way, the manometric switch 24, has two functions here.

The arrangement described is particularly suitable for automatic operation because it is ensured that, while the sample vessel 10 is emptied, neither sample liquid is pressed into the reagent reservoir 16 through the reagent dosing conduit 22 nor, reversely, reagent liquid flows into the sample vessel 10, if inert gas pressure is applied to the sample vessel 10.

The embodiment described herein is considered exemplary and not as limiting as other arrangements and configurations may be made which do not depart from the present invention. Consequently the spirit and scope of the present invention is deemed limited by the appended claims and the reasonable interpretation thereof.

What is claimed is:

1. A device useful for the production of a gaseous measuring sample from a sample liquid and a reagent in a sample vessel and for the transfer of the measuring sample to an atomic absorption spectrometer comprising:
    a sample vessel;
    means defining a pressurized inert gas source to supply pressurized inert gas;
    a gas tight reagent reservoir having a bottom surface therein;
    a connecting conduit leading from said pressurized inert gas source to said reagent reservoir to permit pressure to build up in said reagent reservoir;
    a first stop valve in the connecting conduit between said pressurized inert gas source and said reagent reservoir;
    a plurality of manometric switches connected to said connecting conduit, each of said manometric switches being operable at pressures substantially different from each other and each of said manometric switches being operable at a pressure substantially below the pressure of said inert gas source, said first stop valve being closingly actuated in response to a preselected one of said plurality of manometric switches, means for returning said preselected one of said manometric switches to its initial position when said sample vessel is empty;
    a reagent dosing conduit leading from said bottom surface of said reagent reservoir to said sample vessel and flow therethrough being achieved by the reagent liquid being displaced by said pressurized inert gas;
    a second stop valve disposed in said connecting conduit between said first stop valve and said manometric switches, which is normally closed while the reagent is added, and which is arranged to connect said reagent reservoir to atmosphere to interrupt the delivery of said reagent;
    a flame or measuring cuvette of an atomic absorption spectrometer;
    means to transfer the gaseous measuring sample from said sample vessel to said flame or measuring cuvette of an atomic absorption spectrometer; and
    purging means to purge any remaining sample and reagent liquid from said sample vessel after the transfer of the gaseous measuring sample from said sample vessel.

2. A device as claimed in claim 1 wherein said means to transfer the gaseous measuring sample from said sample vessel to said flame or measuring cuvette of an atomic absorption spectrometer comprises:
    an inert gas feed conduit connected at one end thereof to said connecting conduit and at the other end thereof to said sample vessel for the purpose of feeding inert gas to said sample vessel;
    a third stop valve disposed in said inert gas feed conduit; and
    said means to transfer the gaseous measuring sample including a carrier gas discharge conduit leading from said sample vessel to said flame or measuring cuvette of an atomic absorption spectrometer having a fourth stop valve for closing said carrier gas discharge conduit when transfer of the gaseous measuring sample is complete.

* * * * *

UNITED STATES PATENT AND TRADEMARK OFFICE
CERTIFICATE OF CORRECTION

PATENT NO. : 4,740,356
DATED : April 26, 1988
INVENTOR(S) : Bernhard W. Huber

It is certified that error appears in the above-identified patent and that said Letters Patent is hereby corrected as shown below:

On the title page assignee should read

--(73) Assignee: Bodenseewerk Perkin-Elmer & Co., GmbH, Uberlingen, Federal Republic of Germany --.

Signed and Sealed this

Twenty-eighth Day of March, 1989

Attest:

DONALD J. QUIGG

Attesting Officer

Commissioner of Patents and Trademarks